United States Patent [19]

Gosalvez

[11] 4,384,001

[45] May 17, 1983

[54] TREATMENT OF TUMORS WITH THIAZOLIDINE-4-CARBOXYLIC ACID

[76] Inventor: Mario G. Gosalvez, c/Caleruega 21, 7A Pinar de Chamartin, Madrid, Spain

[21] Appl. No.: 971,729

[22] Filed: Dec. 21, 1978

[51] Int. Cl.³ .......................................... A61K 31/425
[52] U.S. Cl. .................................................. 424/270
[58] Field of Search ........................................ 424/270

[56] References Cited

PUBLICATIONS

Connors et al., Biochem. Pharmacol, 1977, 26(24), pp. 2385-2391.

*Primary Examiner*—Jerome D. Goldberg
*Attorney, Agent, or Firm*—Thomas D. Kiley

[57] ABSTRACT

Described herein is a method of treating malignant tumors or other cancerous conditions with thiazolidine-4-carboxylic acid, or pharmaceutically acceptable salts thereof, to arrest or retard the growth of the tumor. These agents induce reverse transformation in the tumor cells and restore to the cells the property of contact inhibition. A novel process for the preparation of the salts of thiazolidine-4-carboxylic acid is also described.

9 Claims, 2 Drawing Figures

THIAZOLIDINE-4-CARBOXYLIC ACID

TREATMENT OF TUMORS WITH THIAZOLIDINE-4-CARBOXYLIC ACID

FIELD OF THE INVENTION

This invention relates to chemotherapeutic methods for treating malignant tumors or other cancerous conditions.

BACKGROUND

The volume of research directed towards understanding the causes and finding a cure for cancer has greatly increased in the last ten years as a result of increased public concern with the disease. An outgrowth of this research has been the discovery and utilization of a large number of anti-cancer drugs. A common feature of these new drugs is their cytotoxic activity, i.e., they act by killing the cell.

The use of cytotoxic drugs has been a typical first step in the chemotherapeutic treatment of diseases caused by an aggressive cell. This was the case, for example, in the early treatment of tuberculosis, a disease which has now been largely conquered but which was once as dreaded as cancer is today.

As indicated above, cytotoxic agents act by killing cells. Unfortunately, they are not selective and attack healthy or normal cells as well as foreign or diseased ones. Nevertheless, using such agents, skilled specialists were able to add 10-15 years to the life expectancy of persons afflicted with tuberculosis. However, a price had to be paid as the patient suffered terribly from the treatments with these toxic agents. For example, vomiting, hair loss, loss of teeth and other effects had to be endured.

In view of the great shortcomings associated with the use of cytotoxic agents, it could not be said that tuberculosis was curable until non-cytotoxic antibiotic drugs capable of selectively attacking the tuberculosis bacillus became available. Such drugs could be readily used by even general practitioners in relatively simple schemes of treatment. As a result, tuberculosis today has largely been eliminated.

The chemotherapy of cancer is presently limited to cytotoxic drugs that kill normal cells even as they attack the tumor cells. For certain kinds of cancer, skilled specialists using these agents, typically in combinations, have been able to maintain patients relatively free from disease for periods of ten to fifteen years. However, the patient undergoing treatment with these drugs has had to endure great suffering because the cytotoxic agents are severely toxic. Furthermore, the complexity of the treatments preclude their successful use by all but the most highly skilled physicians having access to the best medical facilities. Obviously, many of those who are afflicted with cancer, particularly in underdeveloped countries, do not have access to this kind of treatment. As a result, no one is yet prepared to characterize the limited success achieved using these drugs representing a cure for the cancer involved. That must await the availability of non-toxic drugs that can be readily employed by any physician.

In addition to leading to the discovery of additional cytotoxic agents to be added to the chemical arsenal of anti-cancer drugs, the increased research of recent years has lead to discoveries which are laying the groundwork for a fundamental understanding of the nature of cancer. Out of that research has emerged the concept that the main biological and biochemical differences between a cancer cell and a normal cell are found in the plasma membrane and the cytoskeletal system of contractile microfilaments which connect the plasma membrane with the cell nucleus. It has been postulated that the process by which a normal cell is transformed by a virus or chemical carcinogen to a tumor cell involves a disorganization of the cytoskeletal system of contractile filaments.

Another discovery has been that cancerous cells lack the property of "contact inhibition" that is exhibited by normal cells. Contact inhibition is the property of normal cells when in contact that is manifest by the cessation of cell movement, cell growth and cell division. Because they lack this property, cancer cells when in contact continue to grow and divide. As a result, the cancer cells are highly invasive of adjacent normal tissue. Furthermore, the lack of contact inhibition can result in metastasis, the occurrence of secondary tumors at other body locations caused by tumor cells released into the blood stream.

An important recent discovery has been the observation that tumor cells can be caused to undergo a "reverse transformation" in which the cells take on a morphology akin to that of normal cells in that the cytoskeletal system of contractile filaments in the cells is reorganized and the property of contact inhibition is restored by treatment with dibutyryl cyclic AMP. Cyclic AMP is an agent that naturally occurs in low concentration in cells. However, it serves many cellular functions and, therefore, cannot be administered to humans in a dosage sufficient to restore contact inhibition in cancer cells. This observation has spurred the hope that a specific agent can be found which will induce reverse transformation in cancer cells and restore contact inhibition. Such an agent would be expected to arrest tumor growth and perhaps lead to a slow regression of the tumor by gradual replacement of the tumorous cells with healthy ones.

In view of the state of the art summarized above, one object of the present invention is to provide a new treatment for cancer in mammals, and particularly to treat cancer in humans.

Another object of this invention is to provide a non-cytotoxic chemotherapy for cancer.

Yet another object of this invention is to provide an improved method for causing reverse transformation of cancer cells.

A further object of this invention is to provide a method for imparting the property of contact inhibition to cancer cells.

SUMMARY OF THE INVENTION

The aforementioned objects are provided in accordance with the present invention by administering a dosage of thiazolidine-4-carboxylic acid or a pharmaceutically acceptable salt thereof to an afflicted subject, e.g., a mammal having a malignant tumor or other cancerous condition, in an amount effective to arrest or retard the growth of the tumor, cause reverse transformation of the tumor cells and/or to restore the property of contact inhibition. Administration may be oral or parenteral.

DETAILED DESCRIPTION OF THE INVENTION

Figure 1:
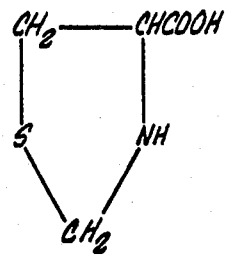
FIG. 1 shows the structural formula of thiazolidine-4-carboxylic acid.

As indicated above, the process of the present invention involves the administration of thiazolidine-4-carboxylic acid, or a pharmaceutically acceptable salt thereof, to a human or other host afflicted with a malignant tumor or other cancerous condition. Thiazolidine-4-carboxylic acid, the structure of which is shown in FIG. 1, is a known compound that has been described in the literature, e.g., in the *Journal of Biological Chemistry*, 227, 393–406 (1957) and in the *Journal of the American Chemical Society*, 59, 200–206 (1937).

A number of diverse utilities have been proposed for this compound. For example, it has been proposed as a component in photographic elements having light insensitive layers (British Pat. No. 1,190,678), and to combat premature aging (British Pat. No. 1,194,383). It has also been proposed to use thiazolidine-4-carboxylic acid as a component in pharmaceutical compositions for treating skin disorders and for use in cicatrization processes (British Pat. No. 1,194,912) and for use in compositions for treating the hair (U.S. Pat. No. 3,243,346). The magnesium salt of thiazolidine-40 carboxylic acid has been suggested as being an effective analgesic agent (U.S. Pat. No. 3,359,166).

I have found unexpectedly that thiazolidine-4-carboxylic acid and its salts can also be used to effectively combat malignant tumors of the kind that afflict humans and other mammals. Although applicant does not wish to be bound by any particular theory, the salts are thought to be useful because they dissociate to the free acid when introduced to the body. Any salt that is pharmaceutically acceptable in an effective amount may be used. In that regard, the salts of thiazolidine-4-carboxylic acid which are most useful in this invention are the pharmaceutically acceptable salts of the alkali metals such as sodium and potassium and the salts of the alkaline earth metals such as magnesium and calcium.

It is presently preferred to employ the sodium salt in the process of this invention since it is readily obtained as a lyophilized powder that is readily soluble in aqueous media and, therefore, well suited for formulation for oral or parenteral administration.

The suitably pure salts of thiazolidine-4-carboxylic acid no matter how derived may be used in the present invention. However, to conveniently obtain the salt as a lyophilized powder, an aqueous solution of thiazolidine-4-carboxylic acid is neutralized to pH of about 7 with concentrated sodium hydroxide or other base selected to provide the desired cation to the salt. The neutralization is conducted in the presence of mannitol or other suitable support for lyophilization. The neutralization should be done as quickly as possible and the solution protected from light during the process. After filtration, the solution is frozen and lyophilized using conventional freeze drying techniques. The resulting dry powder can be reconstituted with water for parenteral injection or used in the preparation of pills for oral administration. This process can also be adapted to the preparation of other salts of thiazolidine-4-carboxylic acid by selection of the appropriate base for neutralization of the acid and has the particular advantage of avoiding hydrolysis to form cysteine and formaldehyde, a common occurrence in other lengthy procedures of preparing salts of thiazolidine-4-carboxylic acid which are known to the prior art.

Tests on mice, rats and dogs have shown thiazolidine-4-carboxylic acid to be completely non-toxic in doses up to 100 mg/kg of body weight. Thiazolidine-4-carboxylic acid and its salts are also non-toxic to humans in doses up to at least 100 mg/kg. Therefore, the dosage administered can vary over a wide range without concern that undesirable side-effects will result from large dosages.

An effective dosage in the process of the present invention may vary, for example, with the kind of malignancy involved. Typically a dosage of from about 1–100 mg/kg of body weight is administered daily for a sufficient time to arrest or retard the growth of the tumor, to induce reverse transformation in malignant tumor cells and to restore the property of contact inhibition to those cells. Preferably, the daily dosage rate will be in the range of from about 5–50 mg/kg of body weight.

While daily administration is preferred, it will be understood that other treatment schedules on other than a daily basis may be suitable in specific situations. As already indicated, the thiazolidine-4-carboxylic agent or a salt thereof can be administered orally, preferably in pill form, or parenterally, by injection of an aqueous solution or by intravenous techniques.

The efficacy of thiazolidine-4-carboxylic acid as a non-cytotoxic agent for treating malignancies is shown by the following experiments.

EXPERIMENTAL RESULTS

Restoration of Contact Inhibition in Colonies of HeLa Cell Using Thiazolidine-4-carboxylic Acid HeLa cells, a type of cell derived from human uterine tumor, were seeded in Eagle culture flasks at the concentration of 50 cells/cm$^2$. The cells were allowed to develop colonies over a 10 day period of culture with 2 changes of medium on the second and sixth day. A tissue culture (minimum essential medium of Eagle with 10% calf serum) comprising amino acids, vitamins and glucose was employed.

Figure 2:
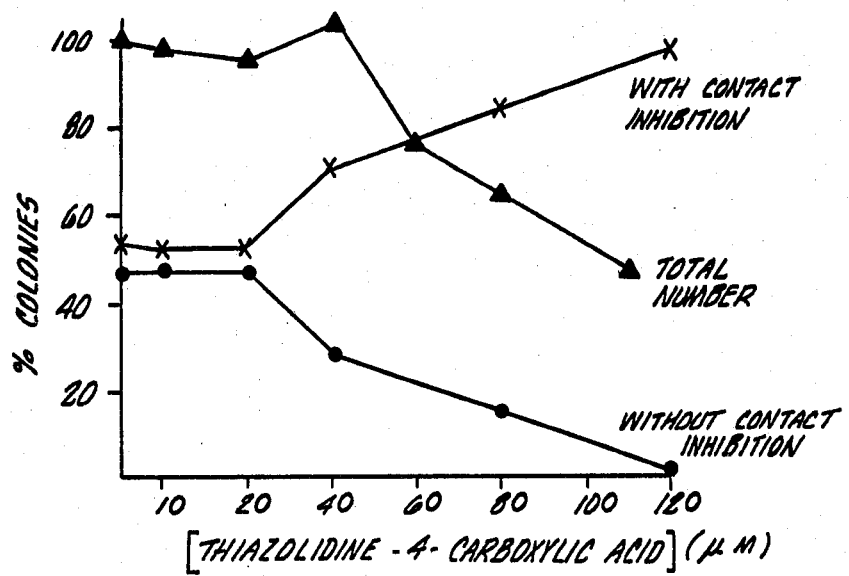
FIG. 2 graphically shows the effect of treating cultures of hela cells with thiazolidine-4-carboxylic acid.

Thiazolidine-4-carboxylic acid neutralized to pH7 with a molar equivalent of sodium hydroxide was added to the medium at varying concentrations on both the second day and the sixth day after the initiation of the culture. A total of 3 flasks containing the cultured colonies were used for each concentration of thiazolidine-4-carboxylic acid employed. On the tenth day, the cells were fixed in neutral formol and were stained with hematoxline. A total of 500 colonies of the same size in each flask were counted at random and the percentage of colonies with contact inhibition (planar morphology) or without contact inhibition (pyrimidal or acuminated morphology) were noted. The results of these experiments are shown in the graph in FIG. 2. As can be seen from that graph, in those cultures which developed in the absence of thiazolidine-4-carboxylic acid, about 50% of the colonies developed without contact inhibition. Those cultures treated with thiazolidine-4-carboxylic acid showed an increased proportion of colonies with contact inhibition. At the maximum dosage, 100% of the colonies showed contact inhibition. This experiment demonstrates that thiazolidine-4-carboxylic acid is able to restore contact inhibition in human tumor cells.

Effect of Thiazolidine-4-Carboxylic Acid On Tumors In Humans

Clinical trials of thiazolidine-4-carboxylic acid have been conducted on 8 patients suffering from advanced metastastic cancer, not amenable to any other treatment. The results of these trials are shown in Table I.

TABLE I

CLINICAL STUDY OF THE EFFECT OF THE SODIUM SALT OF THIAZOLIDINE-4-CARBOXYLIC ACID

| Patients entered diagnosis | Measurable lesion | Total dose received | Toxicity | Response |
| --- | --- | --- | --- | --- |
| ovarian carcinoma | lung | 27 gr | none | stabilization, minor regression (25%) |
| mammary carcinoma | lung | 30 gr | none | progression at slower rate |
| lung adenocarcinoma | lung | 24 gr | none | progression at slower rate |
| lung adenocarcinoma | lung | 18 gr | none | progression at slower rate |
| thyroid carcinoma | lung | 15 gr | none | stabilization |
| lung adenocarcinoma | lung | 6 gr | none | progression at same rate |
| epidermoid (head and neck) | lung | 18 gr | none | stabilization |
| salivary gland carcinoma | lung | 3 gr | none | stabilization |

The trial was designed so that only patients with progressing tumors were admitted and the patients were required to have small lung metastasis whose growth rate was measured by weekly measurements in X-ray plates over several weeks before beginning the treatment.

This kind of patient was selected in order to determine whether administration of thiazolidine-4-carboxylic acid would cause an arrest of tumor growth or a slow down in the rate of growth with eventual regression of tumor size. It was anticipated that tumor reduction, if it occurred, would be at a very slow rate since thiazolidine-4-carboxylic acid is not cytotoxic. Instead, reduction in tumor size would occur by the replacement of tumor cells by normal cells.

Each of the patients were intravenously administered the sodium salt of thiazolidine-4-carboxylic acid, prepared as described above, as an aqueous solution at the dose of 5 mg/kg of body weight on a daily basis.

The patients involved in the trial were afflicted, respectively, with an ovarian carcinoma, a mammory carcinoma, 3 lung adenocarcinomas, a thyroid carcinoma, an epidermoid carcinoma of the head and neck and a salivary gland carcinoma. Each patient had lung metastasis. Table I shows the total doses of thiazolidine-4-carboxylic acid received by each of the patients at the time the evaluation was made. None of the patients showed any toxicity and there were 7 positive responses out of the 8 cases as evaluated by the estimation of the combined area of lung metastasis.

As indicated in Table I, the lung tumor associated with the ovarian carcinoma first showed a stabilization of the tumor at the same size as when the treatment began and this stabilization was followed by a slow regression in the size of the tumor by about 25% of its original size. The lung tumors associated with the thyroid carcinoma, the epidermoid head and neck carcinoma and the salivary gland carcinoma showed stabilization at the size noted when the trial began and had begun to show a tendency towards regression in size. Three other lung tumors, those associated with two lung adenocarcinomas and the mammary carcinoma, showed progression at a slower rate of growth than the rate that the tumor had exhibited up to the beginning of the clinical trials. One of the lung adenocarcinomas was not affected by the treatment and tumor growth progressed throughout the test at the same rate as it had before the trial began.

The results of this study established that thiazolidine-4-carboxylic acid has anti-tumor activity and, therefore, is effective as a non-cytotoxic chemotherapeutic agent for the treatment of cancer.

Effect of Thiazolidine-4-Carboxylic Acid on Mouse Tumors

The effect of thiazolidine-4-carboxylic acid on mouse tumors (leukemia 1210 and Lewis Lung carcinoma) was also tested. In these tests it was found that the drug was completely inactive in increasing the survival time of the mice innoculated with such tumors. However, it is known that the cells associated with those tumors are extremely undifferentiated from normal cells so as to have lost all or nearly all of the cytoskeletal system of contractil microfilaments. Such cells would be expected to be insensitive to agents which induce reverse transformation.

In the foregoing experiments, thiazolidine-4-carboxylic acid was used alone. However, it is within the scope of this invention to employ thiazolidine-4-carboxylic acid as a part of the broader scheme of treatment for cancer. For example, the process of this invention may involve the use of the acid or one of its salts in combination with one or more cytotoxic agents.

The experiments described above demonstrate that thiazolidine-4-carboxylic acid or its salts are effective as non-cytotoxic agents for treating malignancies. The preceding description is but illustrative of the practice of the invention and it is to be understood that other expedients may be employed by those skilled in the art without departure from the scope of the invention which is to be measured by the following claims.

I claim:

1. A process for treating a malignant tumor to arrest or retard the growth thereof comprising administering a member selected from the group consisting of thiazolidine-4-carboxylic acid and a pharmaceutically acceptable salt thereof to a human subject having the malignant tumor according to a dosage schedule effective to arrest or retard the growth of said tumor.

2. A process for treating a malignant tumor comprising administering daily a member selected from the group consisting of thiazolidine-4-carboxylic acid and a pharmaceutically acceptable salt thereof to a human subject having the malignant tumor in an amount from about 1 to about 100 milligrams per kilogram of body weight of said mammal.

3. A process according to claim 2 wherein the member is administered daily in an amount from about 5 to about 50 milligrams per kilogram of body weight of said mammal.

4. A process according to any of claims 1–3 wherein the member is thiazolidine-4-carboxylic acid.

5. A process according to any of claims 1–3 wherein the member is an alkali metal salt of thiazolidine-4-carboxylic acid.

6. A process according to any of claims 1–3 wherein the member is an alkaline earth salt of thiazolidine-4-carboxylic acid.

7. A process according to any of claims 1–3 wherein the member is the sodium salt of thiazolidine-4-carboxylic acid.

8. A process according to any of claims 1–3 wherein the member is administered orally.

9. A process according to any of claims 1–3 wherein the member is administered parenterally.

* * * * *